(12) United States Patent
Becraft et al.

(10) Patent No.: US 12,370,150 B2
(45) Date of Patent: Jul. 29, 2025

(54) AMMONIA PAD WITH RELEASABLE SEAL

(71) Applicants: Matthew Becraft, Annapolis, MD (US); Katherine Becraft, Annapolis, MD (US)

(72) Inventors: Matthew Becraft, Annapolis, MD (US); Katherine Becraft, Annapolis, MD (US)

( * ) Notice: Subject to any disclaimer, the term of this patent is extended or adjusted under 35 U.S.C. 154(b) by 273 days.

(21) Appl. No.: 17/347,256

(22) Filed: Jun. 14, 2021

(65) Prior Publication Data

US 2021/0386681 A1    Dec. 16, 2021

Related U.S. Application Data

(60) Provisional application No. 63/038,140, filed on Jun. 12, 2020.

(51) Int. Cl.
| | |
|---|---|
| A61K 9/70 | (2006.01) |
| A61K 33/02 | (2006.01) |
| A61K 47/32 | (2006.01) |
| A61K 47/38 | (2006.01) |

(52) U.S. Cl.
CPC ............ *A61K 9/7084* (2013.01); *A61K 33/02* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 4,161,283 | A * | 7/1979 | Hyman | A61L 9/12 239/55 |
| 2004/0071759 | A1 * | 4/2004 | Duff | A61M 21/00 424/443 |
| 2007/0031463 | A1 * | 2/2007 | Fotinos | A01N 25/18 424/443 |
| 2007/0243239 | A1 * | 10/2007 | Lanser | A61L 15/46 424/448 |

* cited by examiner

*Primary Examiner* — Isis A Ghali
(74) *Attorney, Agent, or Firm* — Laubscher & Fretwell, P.C.

(57) ABSTRACT

A flexible ammonia pad configured for mounting on the skin of an individual and for sealing and releasing an ammonia inhalant is provided. The pad includes a first flexible impermeable layer having bottom and top surfaces, an adhesive applied to the bottom surface, an ammonia mixture applied to the top surface, and a second flexible impermeable layer covering the top surface. The second layer has at least one outer edge sealed to the first layer and configured to releasably seal the ammonia mixture between the first and second layers. Preferably the ammonia mixture contains 2-15% of ammonia.

2 Claims, 2 Drawing Sheets

AMMONIA PAD WITH RELEASABLE SEAL

This application claims priority in U.S. Provisional Application No. 63/038,140 filed Jun. 12, 2020, the entire contents of which are incorporated herein.

BACKGROUND OF THE DISCLOSURE

The present disclosure relates generally to ammonia inhalants, and more specifically to an ammonia inhalant pad.

Ammonia inhalants, also known as smelling salts, are used to stimulate the senses of an individual, often someone who is unconscious. Such inhalants are typically provided in a capsule-like case that is broken open when the inhalant is to be used.

Such ammonia inhalant capsules are also used by conscious individuals wishing to receive an increased level of stimulation, often when performing high-energy tasks, such as weightlifting or playing a sport.

Though these cases provide an effective mechanism for sealing and storing ammonia inhalants, they can be inconvenient to locate and use when needed. Such capsules are also single use applications. There is thus a need for a multiuse ammonia inhalant application that is more convenient and more easily accessible when needed.

SUMMARY OF THE DISCLOSURE

Accordingly, it is an object of the disclosure to provide a flexible ammonia pad configured for mounting on the skin of an individual and for sealing and releasing an ammonia inhalant. The pad includes a first flexible impermeable layer having bottom and top surfaces, an adhesive applied to the bottom surface, an ammonia mixture applied to the top surface, and a second flexible impermeable layer covering the top surface. The second layer has at least one outer edge sealed to the first layer and is configured to releasably seal the ammonia mixture between the first and second layers. Preferably the ammonia mixture contains 2-15% of ammonia.

In one embodiment of the ammonia pad, the ammonia mixture includes an ammonia solution mixed with a high viscosity methylcellulose to form an ammonia hydrogel. In this embodiment, the second flexible impermeable layer includes a sheet, and the ammonia mixture is encased between the sheet and the first flexible impermeable layer. The sheet preferably includes a bottom surface having a resealable adhesive mounted thereon.

In another embodiment, the second flexible impermeable layer includes a flexible polymer sheet having a plurality of protruding chambers in which the ammonia mixture is contained, and absorbent polymers arranged adjacent to the chambers. Preferably, the polymer sheet includes a high density polyethylene.

BRIEF DESCRIPTION OF THE FIGURES

Other objects and advantages of the disclosure will become apparent from a study of the following specification when viewed in the light of the accompanying drawing, in which.

DETAILED DESCRIPTION

Figure 1:
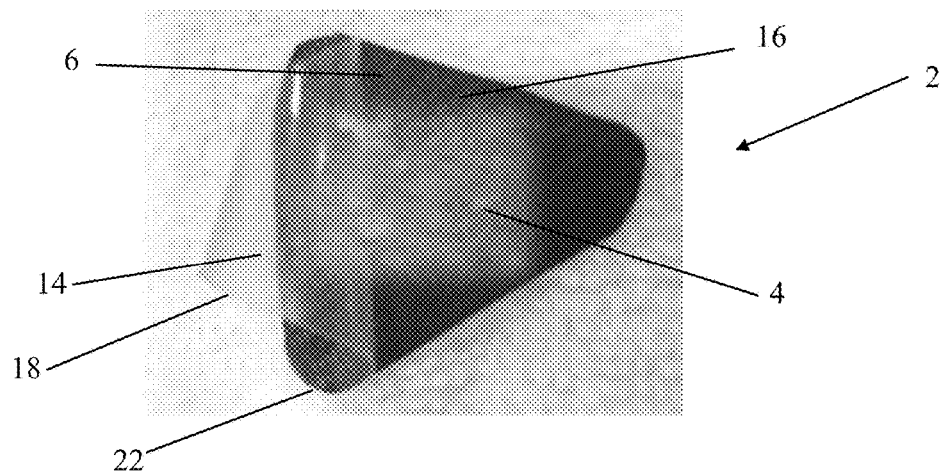
FIG. 1 is a top view of a first embodiment of an ammonia pad according to the present disclosure with the peel layer partially removed.
Figure 2:
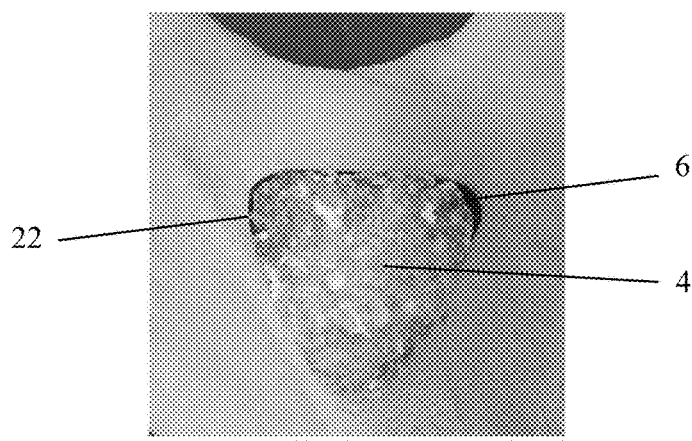
FIG. 2 is a top view of the embodiment of FIG. 1 with the peel layer fully removed.
Figure 3:
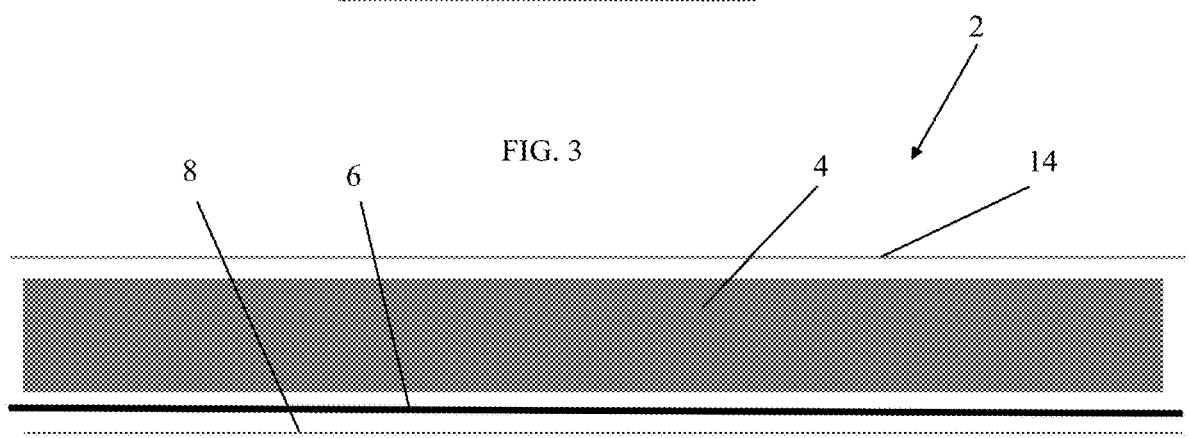
FIG. 3 is a schematic diagram showing the layers of the embodiment of FIG. 1.
Figure 4:
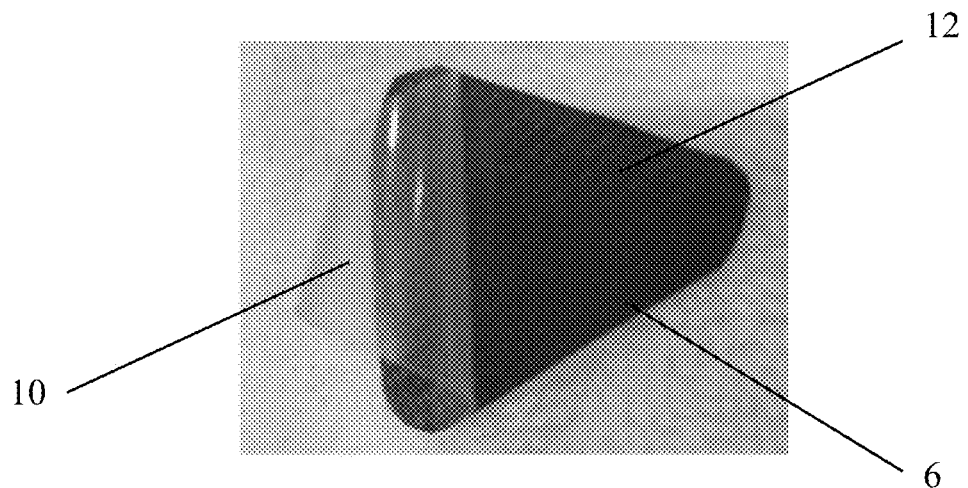
FIG. 4 is a bottom view of the embodiment of FIG. 1 with the adhesive peel layer partially removed.

The present disclosure relates to releasably sealed ammonia pads. FIGS. 1-4 show one embodiment of the pad 2, which includes an ammonia based solution 4 arranged on an impermeable substrate 6 that has an adhesive layer 8 for adhering the substrate to the skin of an individual. A peel strip 10 is arranged on the bottom 12 of the substrate to protect the adhesive layer, and once peeled away, the adhesive is exposed and can be put on an individual's skin to fasten the substrate thereto. A second peel strip 14, preferably a plastic strip, is adhered to the top 16 of the substrate to seal the ammonia based solution. FIG. 1 shows this strip adhered to the substrate, including the strip edges 18 and central portions 20 of the strip. As shown in FIG. 2, the ammonia solution covers nearly the entire top of the substrate. In this instance, the edges 18 of the peel strip 14 would be adhered to the edges 22 of the substrate 6. Preferably, the second peel strip is configured such that it is resealable after removal from the substrate. FIG. 3 shows this embodiment of the ammonia pad once the peel strip 10 has been removed, which includes the bottom adhesive layer 8 followed by the impermeable substrate 6 followed by an ammonia based solution 4 followed by an upper peel strip 14. As is shown, there are no layers between the impermeable substrate 6 and the ammonia solution 4 and no layers between the ammonia solution 4 and the upper peel strip 14. In this embodiment, the substrate and seal strip are triangular is shape with sides of approximately 1.5 inches.

As shown in FIG. 1, the solution 4 is released by peeling back the seal strip 14. Once released, an individual can inhale the solution to receive sensory stimulation that is associated with doing so. Other methods for removing or breaking the pad seal and releasing the ammonia solution, such as through crushing, rupturing, scraping or scuffing the pad, are contemplated, some of which are discussed below. The size and shape of the pad will depend on the desired amount of ammonia on the pad 2, but as noted above, for this embodiment the sides are 1.5 inches in length. The ammonia based solution is prepared by mixing a 2%-15% ammonia, water, ethanol, lidocaine hydrochloride and benzalkonium chloride to create an ammonia based hydrogel, such as Methylcellulose. It will be understood by those with skill in the art that different ammonia solutions can be mixed and applied to the substrate.

The impermeable initial substrate layer 6 is the closest to the skin of an individual. It prevents evaporation and transdermal leaking of the ammonia. Preferably, the material for the substrate forms a support onto which the ammonia solution 4 is cast and to which it will securely bond. For instance, it can include standard commercially available films for medical use such as those supplied by 3M Corporation. Typically such films are made from polyester or the like and may be pigmented or metallized. Preferably, the initial substrate is Scotchpak or 1109 polyester tapes. Alternatively to casting the ammonia solution directly on the initial substrate layer, the ammonia solution may be cast separately and subsequently applied to the substrate layer.

The strength of the adhesive 8 allows the pad to remain on a person's skin for an extended period of time, such as with an adhesive bandage, yet allows the pad to be removed with minimum discomfort and preferably does not give rise to skin irritation, allergic reactions or other dermatological problems. Preferably, a known bio-adhesive, such as an acrylic or silicone based adhesive or polyisobutylene, is used. The adhesive layer also preferably extends along the entire bottom surface 12 of the substrate, but it will be understood by those with skill in the art that it need not extend across the entire surface to provide proper adhesion. The substrate is impermeable to ammonia to ensure the ammonia layer, described below, remains encapsulated.

Figure 5:
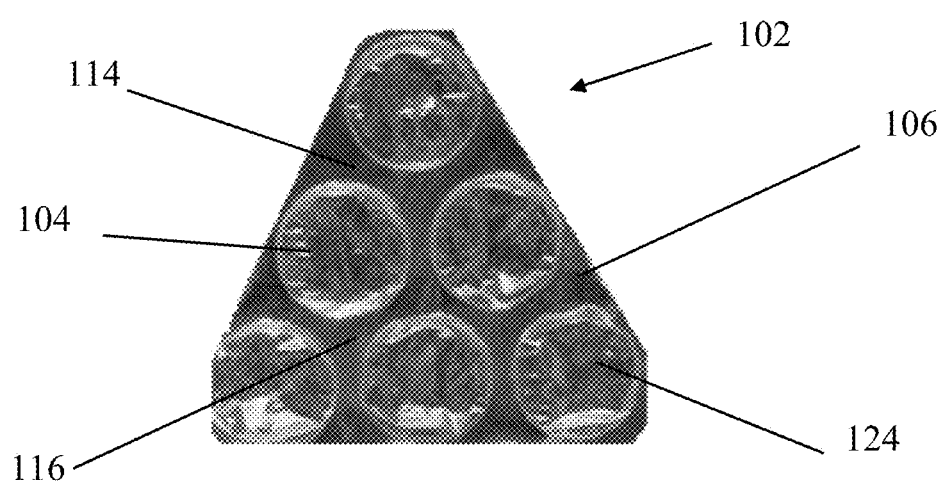
FIG. 5 is a top view of a second embodiment of an ammonia pad according to the present disclosure.
Figure 6:
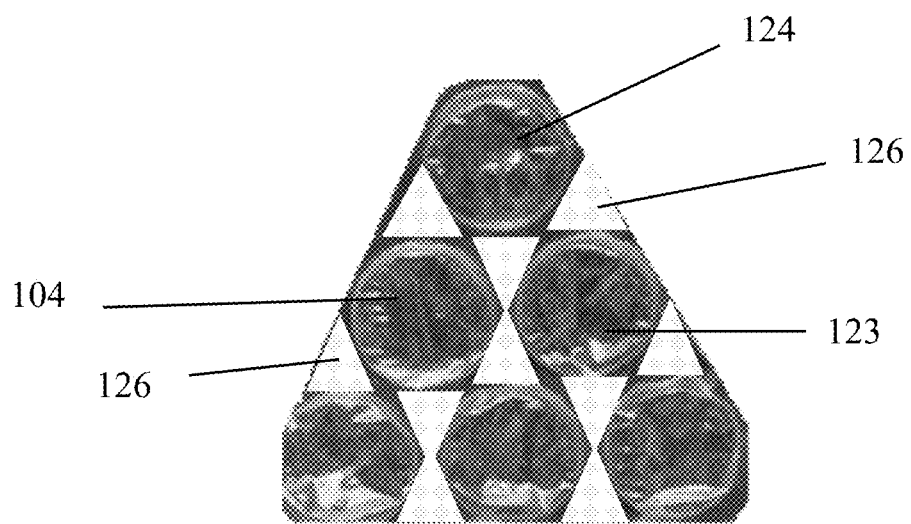
FIG. 6 is a top view of the embodiment of FIG. 5 with a superabsorbent layer.

Referring now to FIGS. 5 and 6, a second embodiment of a releasably sealed ammonia pad 102 is shown. As with the pad of FIGS. 1-4 this pad also includes a bottom adhesive layer (not shown), a substrate 106, an ammonia solution 104, and a top sealing layer 114 that is attached to the top of the substrate 116 to seal the ammonia solution therein. The ammonia solution of this embodiment is contained in chambers 124 affixed to the substrate.

Preferably, the chambers 124 are 0.2 milliliters in size and made of polyethylene. To release the ammonia based solution 104, these chambers are ruptured allowing the solution to be exposed to the surrounding environment. For fluid based solutions, there is a super absorbent material 126 surrounding the chambers, such as amorphous mineral silicate or other superabsorbent polymer, to absorb the ammonia solution when it is released. The super absorbent material is shown in FIG. 6.

In another embodiment, the ammonia based solution is a microencapsulated ammonia based mixture. These microcapsules may include an ammonia based solution alone, or alternatively they may include an ammonia based solution along with a neutral fluid or an aroma enhancing fluid, depending on the desired effect. The neutral microcapsules are included to preserve the integrity of the ammonia containing microcapsules prior to use of the product. The amount of ammonia and non-ammonia microcapsules will depend on the level of ammonia inhalant desired.

The microcapsules that store the ammonia and other solutions are small hollow balls of gelatin or melamine. Preferably, they have a diameter ranging from 22-150 microns, the size of which is determined based on desired strength of each microcapsule.

The technique for microencapsulation can vary. For instance, a methanol-modified melamine-formaldehyde (MMF) resin shell can be used. MMF is more resistant than gelatin. Alternatively, the microcapsules are mixed with a latex solution and dried, or they can be mixed onto the adhesive and sealed. Depending on the application, thicker, more resilient microcapsules are provided, and the addition of a protective layer/solution is also provided. The microcapsules are preferably embedded when a pad substrate paste is prepared and applied to the substrate as with the embodiment of FIGS. 1-4.

The neutral microcapsules have a significantly greater diameter than that of the ammonia capsules. These serve as shock absorbers to protect the microcapsules during storing, transport, and otherwise non-use of the pad.

In another embodiment, interfacial polymerization, anchored in a porous surface/textile, are provided to contain the ammonia based solution. In yet another embodiment, the ammonia solution is formulated in a nonpolar solvent such as hexanes, benzene, and/or some hydrocarbon, that will make the solution hydrophobic and capable of being placed in a water based microcapsule.

Although the above description includes references to particular embodiments, it is to be understood that these embodiments are merely illustrative of the principles and applications of the present disclosure. It is therefore to be understood that numerous modifications may be made to the illustrative embodiments and that other arrangements may be devised and employed without departing from the spirit and scope of the present disclosure.

What is claimed is:

1. A flexible ammonia pad configured for mounting with the skin of an individual, consisting essentially of:
   a. A first flexible impermeable layer having a bottom surface having an adhesive applied thereto and a peel strip arranged thereon, the peel strip releasably sealing the adhesive;
   b. an ammonia mixture arranged on an upper surface of said first flexible impermeable layer, the ammonia mixture including an ammonia solution mixed with a high viscosity methylcellulose to form an ammonia paste; and
   c. a removable second flexible impermeable layer arranged immediately adjacent the ammonia mixture, at least one outer edge of the removable second flexible impermeable layer being sealed to said first flexible impermeable layer, the first flexible impermeable layer and removable second flexible impermeable layer being outer layers of the ammonia pad configured to releasably seal said ammonia mixture between said first and second flexible impermeable layers, the ammonia mixture being the only layer between the first flexible impermeable layer and removable second flexible impermeable layer, whereby when the first flexible impermeable layer is arranged on the hand of an individual and the removable second flexible impermeable layer is removed, the ammonia mixture becomes the uppermost layer of the ammonia pad.

2. A flexible ammonia pad as defined in claim 1, wherein said ammonia mixture contains 2-15% of ammonia.

* * * * *